United States Patent [19]

Sowerby

[11] 4,415,804

[45] Nov. 15, 1983

[54] ANNIHILATION RADIATION ANALYSIS

[75] Inventor: Brian D. Sowerby, Kareela, Australia

[73] Assignee: Australian Atomic Energy Commission, Lucas Hights, Australia

[21] Appl. No.: 213,149

[22] Filed: Dec. 4, 1980

[30] Foreign Application Priority Data

Dec. 20, 1979 [AU] Australia ............................. PE1797

[51] Int. Cl.$^3$ ........................ G01V 5/00; G01N 23/06
[52] U.S. Cl. ....................................... 250/255; 378/53
[58] Field of Search ................... 250/252, 255, 358 R, 250/359, 360, 363 R, 253; 378/45, 53

[56] References Cited

U.S. PATENT DOCUMENTS

| | | | |
|---|---|---|---|
| 3,529,153 | 9/1970 | Zimmerman et al. | 250/363 R |
| 4,090,074 | 5/1978 | Watt et al. | 250/255 |
| 4,224,517 | 9/1980 | Lubecki et al. | 250/255 |
| 4,266,132 | 5/1981 | Marshall | 250/359 |
| 4,278,882 | 7/1981 | Clayton et al. | 250/359 |

FOREIGN PATENT DOCUMENTS

| | | |
|---|---|---|
| 1092956 | 11/1967 | United Kingdom . |
| 1183514 | 3/1970 | United Kingdom . |
| 1298355 | 11/1972 | United Kingdom . |
| 1533268 | 11/1978 | United Kingdom . |

*Primary Examiner*—Alfred E. Smith
*Assistant Examiner*—Janice A. Howell

*Attorney, Agent, or Firm*—Ladas & Parry

[57] ABSTRACT

An apparatus and method for quantitatively measuring the concentration of a first element or group of elements having substantially similar atomic numbers in a matrix comprising other elements having substantially different atomic numbers to that or those of said first element or group of elements is diclosed. The apparatus comprises (i) a source yielding γ-rays, of sufficient energy for pair production;
(ii) detecting means being associated with said source and being capable of detecting 0,511 MeV annihilation radiation;
(iii) first measuring means for making a measurement of or proportional to bulk density;
(iv) shielding means interposed between said source and said detecting means thereby reducing the intensity of direct source γ-rays impinging on said detecting means; and
(v) calculating means associated with the outputs of said detecting means and said measuring means to calculated said concentration;

and wherein said first measuring means is located so as to make said measurement of or proportional to bulk density over substantially the same volume of said matrix as that in which said annihilation radiation originates.

21 Claims, 4 Drawing Figures

ANNIHILATION RADIATION ANALYSIS

The present invention relates to a method and apparatus for the determination of a high atomic number component in a low atomic number matrix or of a low atomic number component in a high atomic number matrix based on the measurement of 0.511 MeV annihilation radiation and bulk density, especially by Compton scattered radiation. The invention finds particular application in the determination of the ash content of coal. Whilst the following description emphasises that aspect of the invention which relates to coal analysis, it will be readily apparent to those skilled in the art that other determinations based on differences in atomic numbers may be made employing the method and apparatus of the present invention.

In its simplest preferred form, a coal sample is irradiated with $\gamma$-rays of energy sufficient for pair production, (i.e. $>1.022$ MeV) and the resulting annihilation and Compton scattered radiation are measured in a shielded detector. Compared to X-ray methods of ash analysis which depend on a single measurement proportional to mass absorption coefficient, the present method has the advantages of: (a) less sensitivity to high atomic number (Z) elements such as iron and calcium, (b) less sensitivity to moisture variations and (c) greater penetration depth because of the higher energies used. The method can accordingly be used for the analysis of a high-Z component in a low-Z matrix or alternatively of a low-Z component in a high-Z matrix.

On-line determination of the ash content of coal is important particularly in coal washing and blending operations that precede its use in steel production and power generation. Even a slight improvement in efficiency of these operations can result in considerable economic savings since coal is used in very large quantities.

Coal consists of coal matter (carbon, hydrogen, oxygen, nitrogen and sulfur) and mineral matter (mainly aluminium and other silicates, and a little iron, sometimes as iron sulfide). Coal ash is the oxidised incombustible residue from combustion of coal, and is closely correlated with the mineral matter content.

Early attempts to determine ash content of coal by radioisotope techniques were based on the atomic number (Z) dependence of $\beta$-, and X-ray interactions and the fact that the mean Z of ash is higher than that of coal matter. X-ray techniques were soon proved superior to $\beta$-ray techniques. In a limited numer of applications, a single measurement proportional to the mass absorption coefficient of X-rays in coal determined ash content with sufficient accuracy. In some cases however, variations in high-Z elements in the ash introduced unacceptable errors. This limitation was later overcome by compensation of the single measurement by iron concentration determined by X-ray fluorescence analysis, as described by Rhodes et al. in Radioisotope Instruments in Industry and Geophysics (Proc. Symp. Warsaw, 1965) 1, I.A.E.A, Vienna (1966), 447., and by Cammack & Balint in A.I.M.E. Annual Meeting, Las Vegas, Nev. (1976) Preprint No. 76-F-24. The main limitations of the compensation technique is that iron K X-rays are strongly absorbed by coal, making sampling and crushing necessary before analysis.

Alternatively, variations in high-Z elements can be compensated by making measurements porportional to mass absorption coefficients of coal at two X-ray energies as described by Fookes et al. in Nuclear Techniques in Exploration, Extraction and Processing of Mineral Resources (proc. Symp. Vienna, 1977) I.A.E.A., Vienna (1977), 167, and in Australian Pat. No. 501 427 in the name of Australian Atomic Energy Commission. However, to achieve adequate penetration into the coal sample, X-ray energies of $>50$ keV required. At these energies the sensitivity of ash variations is low and highly accurate counting is required.

Neutron techniques can be used to measure the concentration of some specific elements in bulk coal samples. Ash can be determined indirectly from the measurement of carbon and hydrogen contents as described in Australian Patent Application No. 39253/78 in the name of Australian Atomic Energy Commission and by Sowerby in Nuclear Instruments and Methods 160, (1979) 173. Alternatively ash can be determined from neutron activation analysis of aluminium and/or silicon in coal. Activation analysis for aluminium is described by Wormald et al. in Internat. Journal of Applied Radiation and Isotopes 30, (1979) 297. However this method involved separate irradiation, decay and counting periods and its accuracy depends on the correlation of Al with ash in the coal.

When a sample is irradiated with gamma rays of energy $>1.022$ MeV, it is possible to produce electron-positron pairs whose total energy is equal to the energy of the incident gamma ray. This process, which is called pair production, only takes place in the field of charged particles, mainly in the nuclear field but also to some degree in the field of an electron. The positron so formed will rapidly lose almost all its energy by collisions with electrons and ions and will subsequently annihilate by colliding with an electron. Both the positron and electron will disappear with the appearance of two oppositely directed $\gamma$-rays of energy 0.511 MeV, the so-called annihilation radiation.

For $\gamma$-ray energies less than about 2 MeV, the total cross section for pair production can be calculated as described by Overbo et al. in Physical Review A8, (1973) 688, from the expression:

$$\sigma = \alpha Z^2 r_o^2 \frac{2\pi}{3} \left( \frac{k-2}{k} \right)^3 \left\{ 1 + \frac{\epsilon}{2} + \frac{23}{40} \epsilon^2 + \frac{11}{60} \epsilon^3 + \frac{29}{960} \epsilon^4 \right\} \quad (1)$$

where $\alpha$ = fine structure constant
$Z$ = atomic number
$r_o = 7.94 \times 10^{-26}$ cm$^2$
$k$ = photon energy in units of $M_e c^2$
$M_e$ = mass of electron $$\epsilon = (2k - 4)/(2 + k + 2\sqrt{2k}).$$

The cross section for pair production increases rapidly with increasing $\gamma$-ray energy. However there are few suitable radio-isotope sources which emit $\gamma$-rays well above the pair production threshold. Some suitable sources are $^{60}$Co(T$_{\frac{1}{2}}$=5.3 years, E$_\gamma$=1.33, 1.17 MeV), $^{228}$Th(T$_{\frac{1}{2}}$=1.9 years, E$_\gamma$=2.62 MeV), $^{124}$Sb(T$_{\frac{1}{2}}$=60 days, E$_\gamma$=1.69 MeV) and $^{226}$Ra(T$_{\frac{1}{2}}$=1620 years, E$_\gamma$=1.76 MeV). Of these, $^{60}$Co and $^{226}$Ra are the most suitable for industrial applications because of their long half-lives and ready availability.

It can be shown that the intensity I of annihilation γ-rays in a backscatter geometry is proportional to the expression:

$$\rho \cdot \exp(-u_i \rho t_i - u_o \rho t_o) \sum_i \left\{ \frac{W_i Z_i^2}{A_i} \right\} \quad (2)$$

where $\rho$=sample density; $u_i$, $u_o$=mass attentuation coefficients for ingoing and outgoing radiation; $t_i$, $t_o$=path lengths in the sample for ingoing and outgoing radiation; $W_i, Z_i$ and $A_i$=weight fraction, atomic number and atomic weight of element i.

The present invention relates to the use of annihilation radiation for elemental analysis. In the present method a sample is irradiated with γ-rays of energy above the pair production threshold and, at the same time, annihilation and Compton scattered radiation are measured. From equation (2) it can be seen that the intensity of annihilation radiation will be approximately proportional to $Z^2/A$ and that density compensation will be required for quantitative analysis.

The present invention provides an apparatus for quantitatively measuring the concentration of a first element or group of elements having substantially similar atomic numbers in a matrix comprising other elements having substantially different atomic numbers to that or those of said first element or group of elements, which apparatus comprises (i) a source yielding γ-rays, of sufficient energy for pair production;

(ii) detecting means being associated with said source and being capable of detecting 0,511 MeV annihilation radiation;

(iii) first measuring means for making a measurement of or proportional to bulk density;

(iv) shielding means interposed between said source and said detecting means thereby reducing the intensity of direct source γ-rays impinging on said detecting means; and (v) calculating means associated with the outputs of said detecting means and said measuring means to calculate said concentration;

and wherein said first measuring means is located so as to make said measurement of or proportional to bulk density over substantially the same volume of said matrix as that in which said annihilation radiation originates.

In another aspect, the invention provides a method for quantitatively determining the concentration of a first element or group of elements having substantially similar atomic numbers in a matrix comprising other elements having substantially different atomic numbers to that or those of said first element or group of elements, which method comprises combining the results of (a) at least one measurement of 0,511 MeV annihilation radiation over a selected volume of said matrix, and (b) at least one measurement of or proportional to bulk density over said selected volume.

Preferably, the measurement of or proportional to bulk density is a measurement of Compton scattered γ-rays, however a measure of volume and mass may also be employed in the practice of the present invention.

In some circumstances, where desired, the accuracy of an analysis done according to the method of or employing the apparatus of the present invention may be improved by combining with the measurement of annihilation radiation and bulk density, one or more measurements of the concentration of an interfering element or group of elements having substantially similar atomic numbers, e.g. the higher atomic number elements of the mineral matter component of coal such as Fe. A suitable further measurement would be that of the shape of the Compton scatter peak.

The detecting means employed in the apparatus of the invention may be a single detector or a number of detectors, the outputs being combined to yield the concentration source.

A further embodiment of the invention provides an apparatus in which the detecting means comprises detectors so located as to detect both oppositely directed annihilation quanta in coincidence, the measured coincidence count rate being combined with a measurement of Compton scattered radiation which may be detected on the same detectors or separately.

Whilst the invention is generally described in its application to the analysis of ash in coal, analyses of iron in iron ores, moisture in soils, organic matter in clay and mineral content of bone also fall within the scope of the present application. Probably the most promising industrial application of the technique is to the bulk analysis of ash in coal.

The apparatus and method of the invention are suitable for measuring the ash content of coal surrounding a borehole.

Calculations have been made to test the sensitivity of the method for the determination of ash in coal. These calculations have assumed a backscatter geometry and a $^{60}$Co source. Coal of composition equal to the mean of all assays of Australian coals quoted by the Joint Coal Board and Queensland Coal Board Report on Australian Black Coals, September 1976, has been assumed. The effect of changes in various parameters is shown in Table 1.

TABLE 1

| Variable | Change Variable From | To | Calculated relative change in intensity of annihilation radiation |
|---|---|---|---|
| Ash | 10.0 | 11.0 wt % (d.b.)* | 0.8% |
| Iron | 0.5 | 0.6 wt % (d.b.)* | 0.16% |
| Water | 0 | 1.0 wt % (a.r.)* | 0.07% |
| Density | 1.00 | 1.10 g cm$^{-3}$ | 2.1% |

*d.b. = dry basis, a.r. = as received basis.

These calculations show that for an application in which ash content was required to within 1 wt % (d.b.), one would need to determine the annihilation radiation intensity to 0.8% relative. Under most circumstances correction for Fe or water variations would not be required.

Compared to the X-ray techniques discussed above, the present method has the advantage of using more penetrating radiation, therefore enabling measurements to be made on larger and therefore more representative coal samples. Also the present method has significantly less sensitivity to Fe variations than the single mass attenuation coefficient high energy X-ray method. Examination of the mass attenuation coefficients of coal, ash and iron for pair production and for 50 keV X-rays shows that the present method is a factor of about 2.5 less sensitive to iron than the single X-ray scatter method.

The correlations between calculated annihilation γ-ray yields and coal parameters have been determined using 112 Australian Coal compositions published by the Joint Coal Board and Queensland Coal Board. The correlations show that ash should be determined to within 0.77 wt % using this method. This compares with errors of about 1.8 wt % ash for uncompensated X-ray methods.

The invention is further described below with reference to the accompanying drawings in which.

Figure 1:
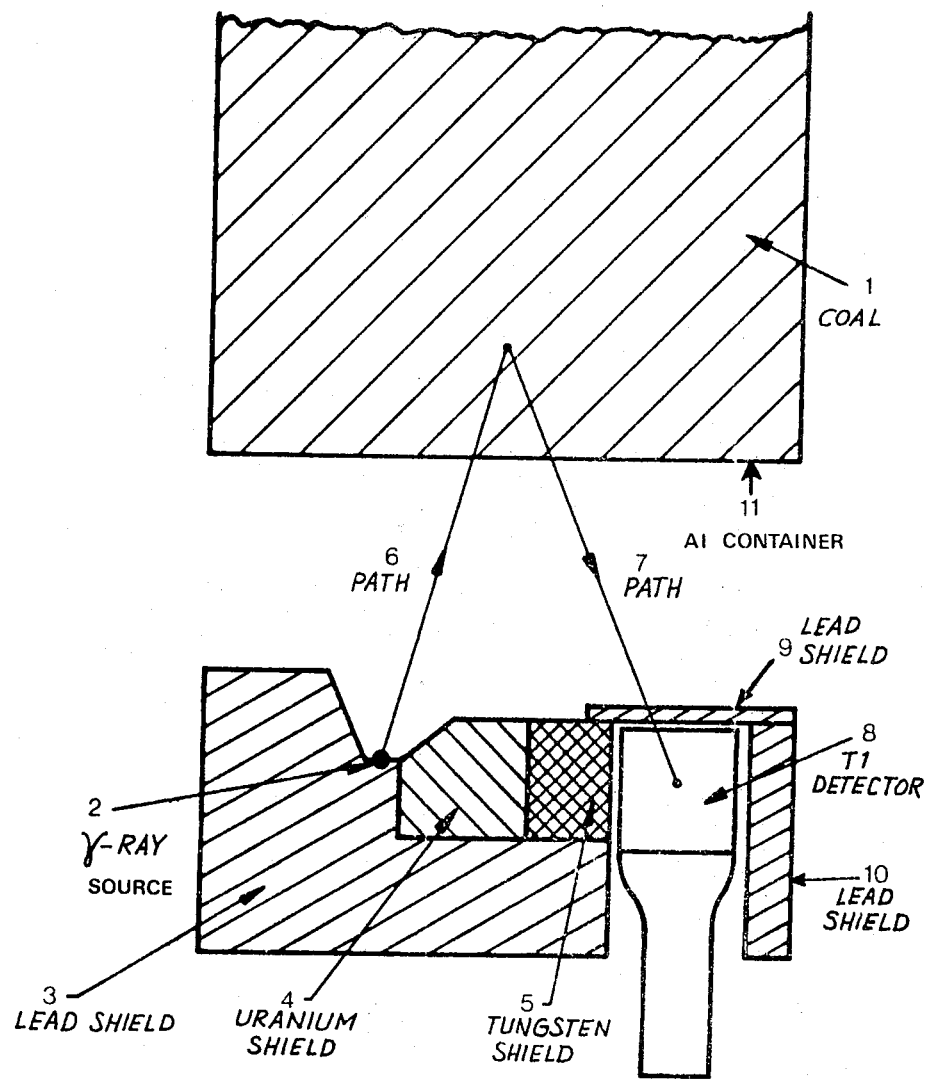
FIG. 1 represents a cross sectional view of a γ-ray backscatter gauge used for determination of annihilation and Compton scatter count rates from bulk coal samples in a preferred form of the invention.
Figure 2:
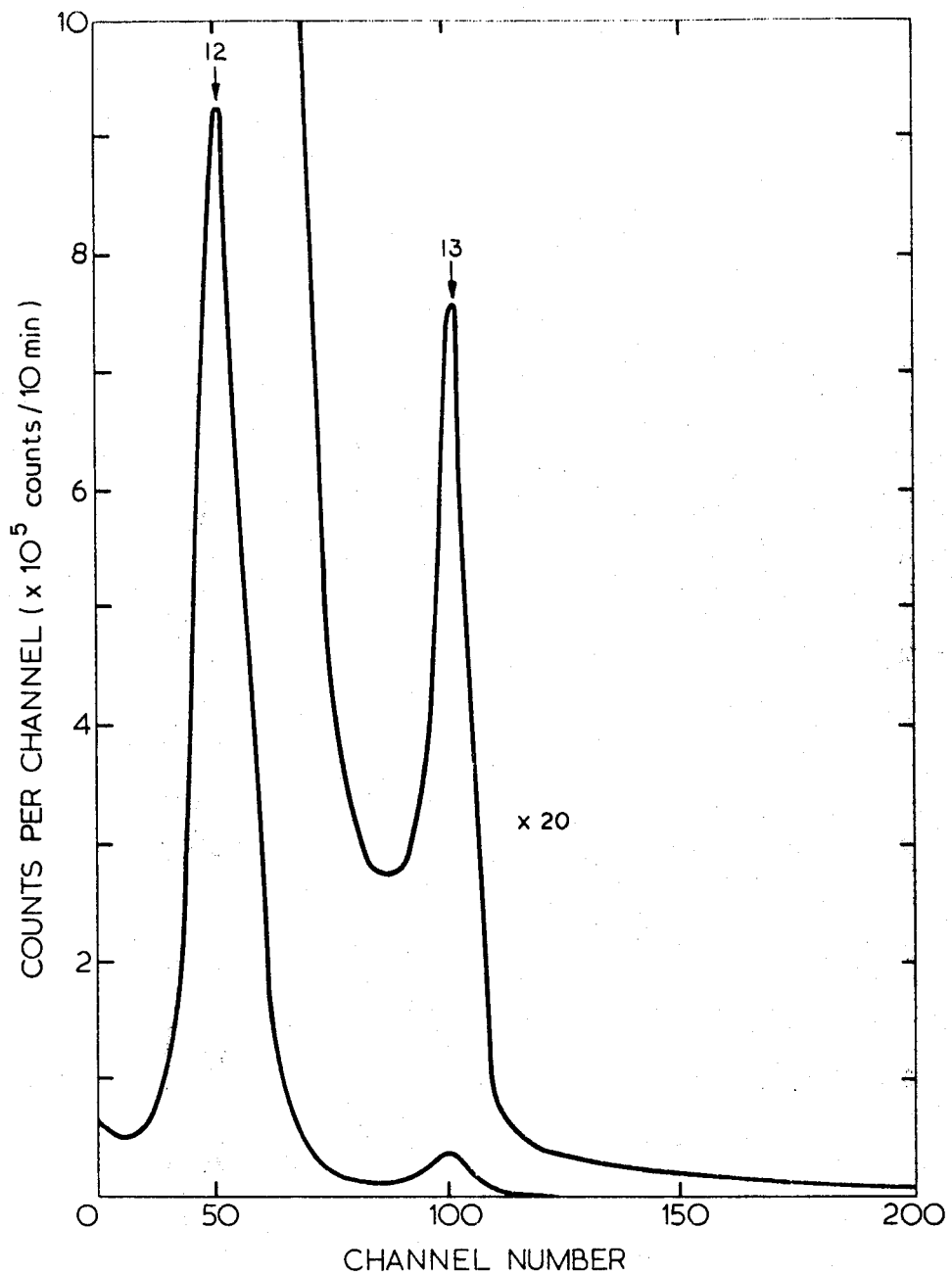
FIG. 2 represents a pulse height spectrum obtained using the γ-ray backscatter guage of FIG. 1 with a coal sample containing 12 wt % ash.
Figure 3:
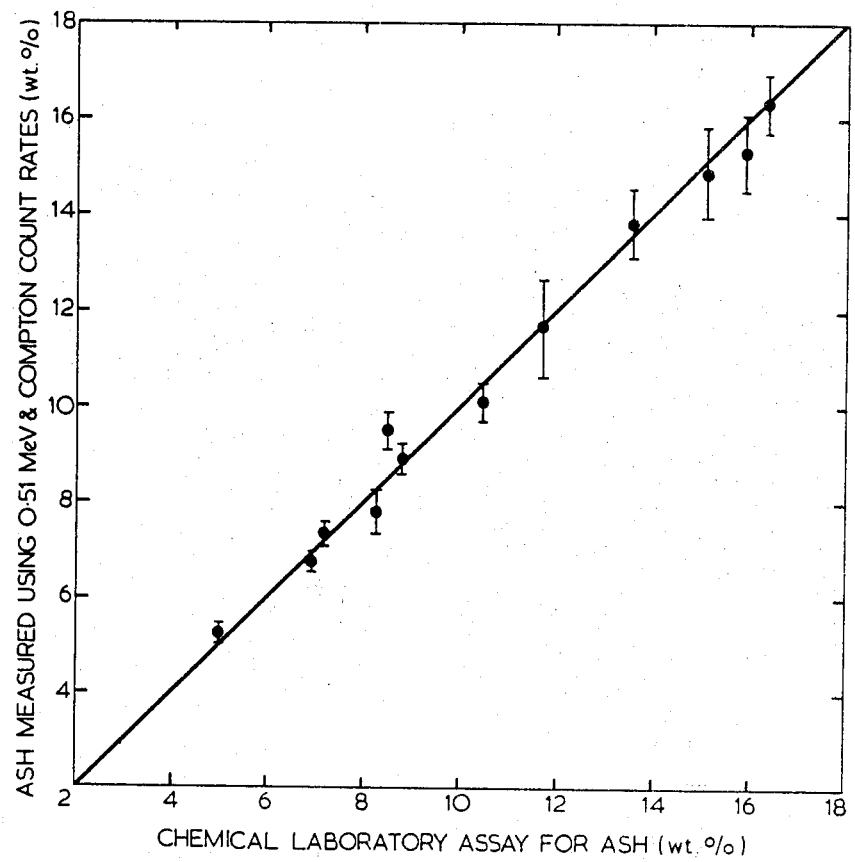
FIG. 3 represents the comparison of chemical laboratory and experimental assays of ash for 13 bulk coal samples with <18 wt % ash from the Utah Blackwater mine. The experimental assays were calculated from the intensities of the 0.511 MeV annihilation γ-rays and Compton scatter γ-rays.

The present method has been tested experimentally using the assembly shown in FIG. 1. Referring to FIG. 1, a coal sample (1) of approximate mass 50 kg is exposed to a 7.4 GBq $^{60}$Co γ-ray source (2) protected by a lead shield (3), a uranium shield (4) and a tungsten shield (5). The source (2) emits γ-rays having a path (6) which result in 0,511 MeV annihilation γ-rays having a path (7) to a 76 mm diameter×76 mm thick sodium iodide (T1) detector (8). The detector (8) is shielded by lead shields (9) and (10) from extraneous radiation. This geometry has been chosen to ensure that the angle for Compton scattering is in excess of about 90° so that the energy of Compton scattered 1.33 MeV γ-rays is below about 0.37 MeV. A typical pulse height spectrum from a coal sample is shown in FIG. 2. In FIG. 2 counts per channel are plotted against channel number which results in a spectrum showing Compton radiation scatter (12) and 0.511 MeV annihilation radiation (13). Count rates measured using a 7.4 GBq $^{60}$Co source were about 700 counts s$^{-1}$ in the 0.511 MeV photopeak (13) and 24000 counts s$^{-1}$ in the Compton scatter peak (12).

Measurements were performed on 57 black coal samples each of about 180 kg from various Australian coalfields. The samples contained from 5.0 to 32.1 wt % ash and from 0.6 to 18.8 wt % Fe in the ash. Sampling was performed acccording to Australian Standard As-1676-1975 and the samples were chemically analysed.

Sub-samples weighing about 50 kg each were placed in Al containers (11) for measurement. At least two sub-samples of each of the 57 bulk coal samples were analysed, both uncompacted and compacted by shaking and/or prodding. RMS deviations between chemical laboratory ash and ash calculated from the annihilation and Compton count rates were between 0.4 and 1.3 wt % ash as shown in Table 2. Ash was calculated using an equation of the form $$\text{Ash} = a.P + b.C + c \ldots \quad (3)$$

where a,b,c=constants, P=mean 0.511 MeV count rate and C=mean Compton scatter count rate.

TABLE 2

| SAMPLES | Ash (wt. %) Mean | Ash (wt. %) Range | Iron in Ash (wt %) Mean | Iron in Ash (wt %) Range | RMS error in ash determination (wt %) |
|---|---|---|---|---|---|
| South Coast (AIS) 15 samples | 17.3 | 10.4–31.3 | 2.5 | 0.6–4.5 | 1.37 |
| Utah Blackwater 24 samples | 16.6 | 5.0–27.8 | 9.0 | 3.2–18.8 | 1.25 |
| Utah Blackwater 12 samples (those with <18 wt. % ash) | 10.6 | 5.0–16.4 | 9.2 | 5.9–12.6 | 0.46 |
| Liddell 18 samples | 26.7 | 21.9–32.1 | 5.2 | 3.3–6.3 | 0.57 |

Measurements were also performed on the assembly in FIG. 1 to determine experimentally the effects of variations in gain, vertical sample movement and moisture. The results of these measurements are summarised in Table 3.

TABLE 3

| Factor | Variation | Measured error in ash |
|---|---|---|
| Gain shift | 0.05% relative | 0.22 wt % |
| Vertical movement of sample | 10.0 mm | <0.4 wt % |
| Moisture | 1.0 wt % | 0.1 wt % |

Potential applications of the invention include the on-line bulk analysis of coal on a conveyor belt or in a chute or hopper, the bulk analysis of coal slurries, the analysis of coal borehole cores and in-situ borehole analysis.

A first preferred embodiment of the invention provides for on-line bulk analysis of ash in coal using an assembly similar to that shown in FIG. 1. This assembly is suitable for the on-line analysis of coal on a conveyor belt or in a chute or hopper. The coal should preferably be of infinite thickness with respect to backscattered radiation (i.e. >20 cm). Possible improvements to this assembly include optimising the source-detector and source-sample distances and adjusting shield thicknesses and detector size. As well it may be desirable to collimate incident and/or scattered radiation to either improve depth response or to improve the matching of the sample volumes for pair production and Compton scattering. A further improvement to the assembly in FIG. 1 can be achieved by using a higher energy γ-ray source such as $^{228}$Th or $^{226}$Ra. The pair production cross section for 2.62 MeV $^{228}$Th γ-rays is about a factor of 15 higher than for the 1.33 MeV $^{60}$Co γ-rays as described by Yamazaki and Hollander in Physical Review 140 (1965) B630. As well, the differential Compton scattering cross section at angles >90° decreases with increasing γ-ray energy. The use of higher γ-ray energy will therefore lead to a much larger ratio of annihilation to Compton γ-rays than was obtained for $^{60}$Co. The use of a higher energy γ-ray source will necessitate changes to the geometry in FIG. 1 such as increased shielding and optimisation of the angle of Compton scattering.

The improvement due to the use of higher energy sources was measured using a 13 MBq $^{228}$Th source and a 920 MBq $^{226}$Ra source in the geometry in FIG. 1. The measured count rates normalised to a 1 GBq source strength, are given in Table 4 for a coal sample containing 18.7 wt. % ash. However, a $^{228}$Th source of activity 1 GBq or greater is difficult to obtain and it is likely that $^{226}$Ra will prove to be the most satisfactory alternative source.

Further improvements in gauge performance can be obtained by increasing the size of the NaI(Tl) detector. Count rates obtained with a 1 GBq $^{226}$Ra source in a backscatter assembly similar to that shown in FIG. 1 but using a 15 cm $\phi \times$ 10 cm NaI(Tl) detector are given in Table 4. With this assembly, a counting time of <5 min will be required to determine ash to ±0.5 wt. %.

TABLE 4

| | | Count rates (counts/s) | |
|---|---|---|---|
| Source | Geometry | 0,511 MeV photopeak | Compton scatter peak |
| $^{60}$Co | FIG. 1 | 95 | 3240 |
| $^{226}$Ra | FIG. 1 | 217 | 1710 |
| $^{228}$Th | FIG. 1 | 431 | 1560 |
| $^{226}$Ra | 15 cm × 10 cm NaI (Tl) | 936 | 17130 |

In the present work, measurements have been made in a backscatter geometry in which the sample is infinitely thick with respect to backscatter radiation (i.e. >25 cm). However, because of the close matching of annihilation and Compton radiation as a function of sample depth, errors in measurements with thinner samples are not great. For samples of thickness >19 cm, uncorrected ash values will be in error by less than 1 wt. % and even for samples of thickness between 12 and 19 cm, ash errors will not exceed 3 wt. %. Separate depth measurements could be used to correct these values if necessary.

Figure 4:
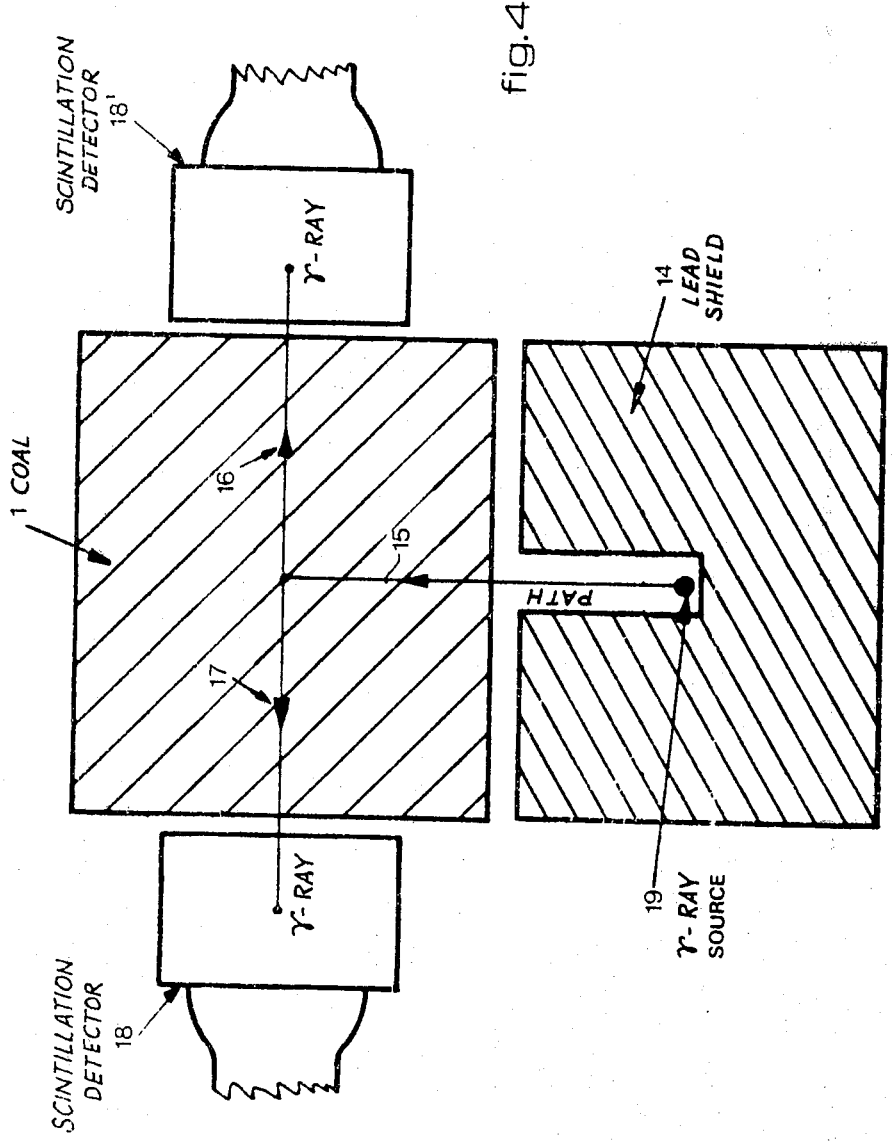
FIG. 4 is a schematic diagram of an assembly for measurement of Compton scatter count rates and of annihilation radiation from a coal sample based on coincidence between oppositely directed 0.511 MeV γ-rays in an alternative preferred form of the invention.

A second preferred embodiment of the invention provides for on-line bulk analysis of ash in coal using a coincidence timing technique similar to that illustrated in FIG. 4. In FIG. 4 a coal sample (1) is exposed to γ-rays from a source (19) encased in a lead shield (14). The γ-rays follow path (15) to the coal sample (1) where they produce two oppositely directed 0.511 MeV γ-rays (16) and (17) which are detected by scintillation detectors (18) and (18'). This application is based on the fact that two oppositely directed 0.511 MeV γ-rays are emitted whenever a positron annihilates. If very fast scintillation detectors are used (e.g. plastic phosphors) very good discrimination of 0.511 MeV γ-rays against background Compton scatter can be obtained. The Compton scatter count rate is measured either simultaneously in one of the detectors (18') or separately using a matched volume scatter or transmission gauge.

What I claim is:

1. Apparatus for quantitatively measuring the concentration of at least a first element, selected from an elemental group consisting of elements having substantially similar atomic numbers, in a matrix comprising other elements having substantialy different atomic numbers to those of said elemental group, which apparatus comprises
   (i) a source yielding γ-rays, of sufficient energy for pair production;
   (ii) detecting means being associated with said source for detecting 0,511 MeV annihilation radiation;
   (iii) first measuring means for making a measurement indicative of bulk density;
   (iv) shielding means interposed between said source and said detecting means thereby reducing the intensity of direct source γ-rays impinging on said detecting means; and
   (v) calculating means associated with the outputs of said detecting means and said measuring means to calculate said concentration; and wherein said first measuring means is located so as to make said measurement indicative of bulk density over substantially the same volume of said matrix as that in which said annihilation radiation originates.

2. Apparatus as defined in claim 1 wherein said detecting means is arranged to detect Compton scattered γ-rays originating in substantially the same volume of said matrix as said annihilation radiation, thereby forming said first measuring means.

3. Apparatus as defined in claim 1 wherein said first measuring means comprises means to measure volume and means to measure mass.

4. Apparatus as defined in any one of claims 1 to 3 further comprising at least one second measuring means which makes measurements of the concentration of at least one interfering element selected from an elemental group consisting of elements having substantially similar atomic numbers, the output of said second measuring means being associated with said calculating means in order to improve accuracy.

5. Apparatus as defined in claim 2 further comprising at least one second measuring means which makes measurements of the concentration of at least one interfering element selected from an elemental group consisting of interfering elements having substantially similar atomic numbers, the output of said second measuring means being associated with said calculating means in order to improve accuracy, and wherein second measuring means further measures the shape of the Compton scatter peak.

6. Apparatus according to any one of claims 1 to 3 wherein said detecting means comprises a plurality of detectors, the outputs of said detectors being combined.

7. Apparatus as defined in any one of claims 1 to 3 wherein said detecting means comprises a single detector.

8. Apparatus as defined in any one of claims 1 to 3 wherein said detecting means comprises detectors so located as to detect both oppositely directed annihilation quanta in coincidence.

9. Apparatus as defined in any one of claim 1 to 3 wherein said elemental group consists of elements, in coal, of high atomic number which comprise the mineral matter of coal and wherein said other elements are those of low atomic number which comprise the coal matter of coal.

10. Apparatus as defined in claim 9 further comprising at least one second measuring means which makes measurements of the concentration of at least one interfering element selected from an elemental group consisting of interfering elements having substantially similar atomic numbers, the output of second said measuring means being associated with said calculating means in order to improve accuracy, and wherein said second measuring means measures the concentration of at least one higher atomic number element of said mineral matter.

11. Apparatus as defined in claim 10 wherein said higher atomic number element is Fe.

12. A method for quantitatively determining the concentration of at least a first element, selected from an elemental group consisting of elements having substantially similar atomic numbers, in a matrix comprising other elements having substantially different atomic numbers to those of said elemental group, which method comprises combining the results of (a) at least one measurement of 0,511 MeV annihilation radiation over a selected volume of said matrix, and (b) at least one measurement indicative of bulk density over said selected volume.

13. The method as defined in clam 12 wherein said measurement of bulk density is a measurement of Compton scattered γ-rays.

14. The method as defined in claim 12 wherein said measurement of bulk density is a measurement of volume and mass.

15. The method as defined in any one of claims 12 to 14 further comprising combining with the results of (a) and (b), the result of (c) at least one further measurement of the concentration of at least one interfering element selcted from an elemental group consisting of interfering elements having substantially similar atomic numbers over said selected volume.

16. The method as defined in claim 13 further comprising combining with the results of (a) and (b), the result of (c) at least one further measurement of the concentration of at least one interfering element selected from an elemental group consisting of interfering elements having substantially similar atomic numbers over said selected volume, and wherein said further measurement is a measure of the shape of the Compton scatter peak.

17. The method as defined in any one of claims 12 to 14 wherein said measurement of 0,511 MeV annihilation radiation is a measure of both oppositely directed annihilation quanta.

18. The method as defined in any one of claims 12 to 14 wherein said elemental group consists of elements, in coal, of high atomic number which comprise the mineral matter of coal and wherein said other elements are those of low atomic number which comprise the coal matter of coal.

19. The method as defined in claim 18 further comprising combining with the results of (a) and (b), the result of (c) at least one interfering element selected from an elemental group consisting of interfering elements having substantially similar atomic numbers over said selected volume, and wherein said further measurement is a measurement of the concentration of at least one higher atomic number element of said mineral matter.

20. The method as defined in claim 19 wherein said higher atomic number element is Fe.

21. The method as defined in claim 17 wherein ash content of coal surrounding a borehole is measured.

* * * * *